US006060592A

United States Patent [19]
Acevedo et al.

[11] Patent Number: 6,060,592
[45] Date of Patent: May 9, 2000

[54] PYRIMIDINE NUCLEOSIDE COMPOUNDS AND OLIGONUCLEOSIDE COMPOUNDS CONTAINING SAME

[75] Inventors: Oscar L. Acevedo, San Diego, Calif.; Martin G. Dunkel, Göttingen, Germany; Phillip Dan Cook, Carlsbad, Calif.

[73] Assignee: ISIS Pharmaceuticals, Inc., Carlsbad, Calif.

[21] Appl. No.: 08/212,006

[22] Filed: Mar. 11, 1994

Related U.S. Application Data

[63] Continuation-in-part of application No. 08/003,487, Jan. 12, 1993, abandoned, which is a continuation-in-part of application No. PCT/US91/00243, Jan. 11, 1991, which is a continuation-in-part of application No. 07/463,358, Jan. 11, 1990, abandoned.

[30] Foreign Application Priority Data

Jan. 11, 1991 [WO] WIPO ............... PCT/US91/00243

[51] Int. Cl.$^7$ .......................... C07H 19/06; C07H 21/00
[52] U.S. Cl. .................. 536/23.1; 536/22.1; 536/25.3; 536/25.32; 536/26.8; 536/28.1; 536/28.4; 536/28.5; 536/28.51; 536/28.52; 536/28.53; 536/28.54; 536/28.55
[58] Field of Search ................... 536/22.1, 23.1, 536/25.3, 25.32, 26.8, 28.1–28.55, 22.3; 514/43, 885, 49, 50

[56] References Cited

U.S. PATENT DOCUMENTS

| | | | |
|---|---|---|---|
| 3,755,295 | 8/1973 | Verheyden et al. | 260/211.5 |
| 3,975,374 | 8/1976 | Hunter et al. | 536/23 |
| 4,210,638 | 7/1980 | Greer | 424/180 |
| 5,250,673 | 10/1993 | Fujii et al. | 536/28.55 |

OTHER PUBLICATIONS

Agrawal et al., "Oligodeoxynucleoside phosphoramidates and phosphorothioates as inhibitors of human immunodeficiency virus," *Proc. Natl. Acad. Sci. USA*, 85:7079–7083, 1988.

Agarwal et al., "Synthesis and enzymatic properties of deoxyribooligonucleotides containing methyl and phenylphosphonate linkages," *Nucl. Acids Res.*, 6:3009–3024, 1979.

Agris et al., "Inhibition of Vesicular Stomatitis Virus Protein Synthesis and Infection by Sequence–Specific Oligodeoxyribonucleoside Methylphosphonates," *Biochemistry*, 25:6268–6275, 1986.

Beaucage et al., "Advances in the Synthesis of Oligonucleotides by the Phosphoramidite Approach," *Tetrahedron*, 12:2223–2311, 1992.

Bielinska et al., "Regulation of Gene Expression with Double-Stranded Phosphorothioate Oligonucleotides," *Science*, 250:997–1000, 1990.

Biggadike et al., "Short Convergent Route to Homochiral Carbocyclic 2'–Deoxynucleosides and Carbocyclic Ribonucleotides," *J. Chem. Soc. Chem. Commun.*, 1083–1084, 1987.

Brill et al., "Synthesis of Oligodeoxynucleoside Phosphorodithioates via Thioamidites," *J. of Amer. Chem. Soc.*, 111:2321–2322, 1989.

Buys et al., "Conformation of Non–Aromatic Ring Compounds," *Recueil*, 1089–1099, 1970.

Castle et al., "Imidazol [4,5–d]pyridazines. I. Synthesis of 4,7–Disubstituted Derivatives," *J. Org. of Chem.*, 23:1534–1538, 1958.

Cazenave et al., "Enzymatic amplification of translation inhibition of rabbit β–globin mRNA mediated by anti–messenger oligodeoxynucleotides covalently linked to intercalating agents," *Nucl. Acids Res.*, 15:4717–4736, 1987.

Constant et al., "Heterodimeric Molecules Including Nucleic Acid Bases and 9–Aminoacridine. Spectroscopic Studies, Conformations, and Interactions with DNA," *Biochemistry*, 27:3997–4003, 1988.

Christescu, "AS–Triazine Derivatives with Potential Therapeutic Action. XIV." *Rev. Roumaine Chim.*, 20:1287–1293, 1975.

Denny, "DNA–intercalating ligands as anti–cancer drugs: prospects for future design," *Anti–Cancer Drug Design*, 4:241–263, 1989.

Dreyer et al., "Sequence–Specific cleavage of single–stranded DNA: Oligodeoxynucleotide–EDTA•FeE(II)," *Proc. Natl. Acad. Sci. USA*, 82:968–972, 1985.

Fox et al., "Thiation of Nucleosides. II. Synthesis of 5–Methyl-2'–deoxycytidine and Related Pyrimidine Nucleosides," *J. of the Amer. Chem. Soc.*, 81:178–187, 1959.

Freskos, "Synthesis of 2'–Deoxypyrimidine Nucleosides Via Copper (I) Iodide Catalysis," *Nucleosides and Nucleotides*, 8:1075–1076, 1989.

(List continued on next page.)

*Primary Examiner*—James O. Wilson
*Attorney, Agent, or Firm*—Woodcock Washburn Kurtz Mackiewicz & Norris, LLP

[57] ABSTRACT

Novel 2- and 4-substituted pyrimidine nucleosides and oligonucleosides are provided, as are methods and intermediates useful in preparing same. In preferred embodiments, one of the 2- and 4-substituents is =O, =NH, or =NH$_2{}^+$ and the other is Q, =C (R$_A$)—Q, C(R$_A$)(R$_B$)—C(R$_C$)(R$_D$)—Q, C (R$_A$)=C(R$_C$)—Q or C≡C—Q, where R$_A$, R$_B$, R$_C$ and R$_D$ independently are H, SH, OH, NH$_2$, or C$_1$–C$_{20}$ alkyl, or one of (R$_A$)(R$_B$) or (R$_C$)(R$_D$) is =O, and Q is halogen, hydrogen, C$_1$–C$_{20}$ alkyl, C$_1$–C$_{20}$ alkylamine, C$_1$–C$_{20}$ alkyl-N-phthalimide, C$_1$–C$_{20}$ alkylimidazole, C$_1$–C$_{20}$ alkylbis-imidazole, imidazole, bis-imidazole, amine, N-phthalimide, C$_2$–C$_{20}$ alkenyl, C$_2$–C$_{20}$ alkynyl, hydroxyl, thiol, keto, carboxyl, nitrates, nitro, nitroso, nitrile, trifluoromethyl, trifluoromethoxy, O-alkyl, S-alkyl, NH-alkyl, N-dialkyl, O-aralkyl, S-aralkyl, NH-aralkyl, azido, hydrazino, hydroxylamino, isocyanato, sulfoxide, sulfone, sulfide, disulfide, silyl, O-(hydroxyl protecting group), a leaving group, a heterocycle, an intercalator, a reporter molecule, a conjugate, a polyamine, a polyamide, a polyethylene glycol, a polyether, or a depurination enhancing group.

44 Claims, 1 Drawing Sheet

OTHER PUBLICATIONS

Gait, *Oligonucleotide Synthesis*, IRL Press, 1985.

Goodchild, "Conjugates of Oligonucleotides and Modified Oligonucleotides: A Review of Their Synthesis and Properties," *Bioconjugate Chemistry*, 1:165–187, 1990.

Habener et al., "5–Fluorodeoxyuridine as an alternative to the synthesis of mixed hybridization probes for the detection of specific gene sequences," *Proc. Natl. Acad. Sci. USA*, 85:1735–1739, 1988.

Inoue et al., "Synthesis and hybridization studies on two complementary studies on two complementary nona(2'-O-methyl) ribonucleotides," *Nucleic Acids Res.*, 15:6131–6148, 1987.

Jager et al., "Oligonucleotide N–alkylphosphoramidates: Synthesis and Binding to Polynucleotides," *Biochemistry*, 27:7237–7246, 1988.

Jayaraman et al., "Selective inhibition of *Escherichia coli* protein synthesis and growth by nonionic oligonucleotides complementary to the 3' end of 16S rRNA," *Proc. Natl. Acad. Sci. USA*, 78:1537–1541, 1981.

Jones, "Preparation of Protected Deoxyribonucleosides," *Oligonucleotide Synthesis: A Practical Approach*, Gait, ed., IRL Press: Washington, Chapter 2, 1985.

Jones et al., "4'–Substituted Nucleosides. 5. Hydroxymethylation of Nucleoside 5'–Aldehydes," *J. Org. Chem.*, 44:1309–1317, 1979.

Kazimierczuk et al., "Synthesis of 2'–Deoxytubercidin, 2'–Deoxyadenosine, and related 2'–Deoxynucleosides via a Novel Direct Stereospecific Sodium Salt Glycosylation Procedure," *J. Am. Chem. Soc.*, 106:6379–6382, 1984.

Knorre et al., "Complementary–Addressed (Sequence–Specific) Modification of Nucleic Acids," *Progress in Nucleic Acid Research and Molecular Biology*, 32:291–320, 1985.

Kunieda et al., "Preparation and Photochemistry of 5,6–Cyclopropyluridines and of Bicyclic Isomers of Thymines," *J. Amer. Chem. Soc.*, 91:7751–7752, 1969.

Le Doan et al., "Sequence–targeted chemical modifications of nucleic acids by complementary oligonucleotides covalently linked to porphyrins," *Nucl. Acids Res.*, 15:8643–8659, 1987.

Letsinger et al., "Effects of Pendant groups at phosphorus on binding properties of d–ApA analgues," *Nucl. Acids Res.*, 14:3487–3499, 1986.

Loose–Mitchell, "Antisense nucleic acids as a potential class of pharmaceutical agents," *TIPS*, 9:45–47, 1988.

Marcus–Sekura, "Techniques for Using Antisense Oligodeoxyribonucleotides to Study Gene Expression," *Anal. Biochemistry*, 172:289–295, 1988.

Marcus–Sekura et al., "Comparative inhibition of chloramphenicol acetyltransferase gene expression by antisense oligonucleotide analogues having alkyl phosphortriester, methylphosphonate and phosphorothioate linkages," *Nucl. Acids Res.*, 15:5749–5763, 1987.

Matsukura et al., "Phosphorothioate analogs of oligodeoxynucleotides: Inhibitors of replication and cytopathic effects of human immunodeficiency virus," *Proc. Natl. Acad. Sci. USA*, 84:7706–7710, 1987.

Meyer, Jr., "Efficient, Specific Cross–Linking and Cleavage of DNA by Stable, Synthetic Complementary Oligodeoxynucleotides," *Journal of the Amer. Chem. Soc.*, 111:8517–8519, 1989.

Miller et al., "A new approach to chemotherapy based on molecular biology and nucleic acid chemistry: Matagen (masking tape for gene expression)," *Anti–Cancer Drug Design*, 2:117–128, 1987.

Miller et al., "Synthesis and Properties of Adenine and Thymine Nucleoside Alkyl Phosphotriesters, the Neutral Analogs of Dinucleoside Monophosphates," *J. of Amer. Chem. Soc.*, 93:6657–6665, 1971.

Miller et al., "Biochemical and Biological Effects of Non-ionic Nucleic Acid Methylpohosphonates," *Biochemistry*, 20:1874–1880, 1981.

Outten et al., "Synthetic 1–Methoxybenzo [d] naptho [1,2–b]pyran–6–one C–Glycosides," *J. of Org. Chem.*, 52:5064–5066, 1987.

Piccirilli et al., ". A Direct Route to 3–(D–Ribofuranosyl)pyridine Nucleosides," *Helvetica Chimica Acta*, 74:397–406, 1991.

Robins et al., "Nucleic Acid Related Compounds. 42. A General Procedure for the Efficient Deoxygenation of Secondary Alcohols. Regiospecific and Stereoselective Conversion of Ribonucleosides to 2–'–Deoxynucleosides," *J. Amer. Chem. Soc.*, 105:4059–4065, 1983.

Roelen et al., "Synthesis of nucleic acid methylphosphonothioates," *Nucl. Acids Res.*, 16:7633–7645, 1988.

Rosenthal et al., "Synthesis of 2–(and 6) –Dithian–2–Yluracil Nucleosides and their Conversion into Nucleoside Derivatives," *Carbohydr. Res.*, 78:33–52, 1980.

Ruby et al., "An Early Hierarchic Role of U1 Small Nuclear Ribonucleoprotein in Spliceosome Assembly," *Science*, 242:1028–1035, 1988.

Sigman, "Nuclease Activity of 1,10–Phenanthroline–Copper Ion," *Accounts in Chem. Res.*, 19:180–186, 1986.

Smith et al., "Antiviral effect of an oligo(nucleoside methylphosphonate) complementary to the splice junction of herpes simplex virus type 1 immediate early pre–mRNAs 4 and 5," *Proc. Natl. Acad. Sci. USA*, 83:2787–2791, 1986.

Stein et al., "Oligodoxynucleotides as Inhibitors of Gene Expression: A Review," *Cancer Research*, 48:2659–2668, 1988.

Stein et al., "Physiochemical properties of phosphorothioate oligodeoxynucleotides," *Nucleic Acids Res.*, 16:3209–3221, 1988.

Suciu et al., "Synthesis of 9–(2, 5–dideoxy–β–glycero–pent–4–enofuranosyl) adenine," *Carb. Research*, 44:112–115, 1975.

Tidd et al., "Evaluation of N–ras oncogene anti–sense, sense and nonsense sequence methylphosphonate oligonucleotide analogues," *Anti–Cancer Drug Design*, 3:117–127, 1988.

Van der Krol et al., "Modulation of Eukaryotic Gene Expression by Complementary RNA or DNA Sequences," *BioTechniques*, 6:958–976, 1988.

Vorbruggen et al., "C–Substitution of Nucleosides with the Aid of the Eschenmoser Sulfide Contraction," *Angew. Chem. Int. Ed.*, 15:689–690, 1976.

Vorbruggen et al., "Nucleoside Synthesis with Trimethylsilyl Triflate and Perchlorate as Catalysts," *Chem. Ber.*, 114:1234–1255, 1981.

Walder, "Antisense DNA and RNA: progress and prospects," *Genes & Development*, 2:502–503, 1988.

Walder et al., "Role of RNase H in hybrid–arrested translation by antisense oligonucleotides," *Proc. Natl. Acad. Sci. USA*, 85:5011–5015, 1988.

Wu et al., "Inhibition of in vitro transcription by specific double–stranded oligodeoxyribonucleotides," *Gene*, 89:203–209, 1990.

Yeung et al., "Photoreactivities and Thermal Properties of Psoralen Cross–Links," *Biochemistry*, 27:2304–3210, 1988.

Zon, "Oligonucleotide Analogues as Potential Chemotherapeutic Agents," *Pharm. Res.*, 5:539–549, 1988.

Zon, "Synthesis of Backbone–Modified DNA Analogues for Biological Applications," *J. of Protein Chem.*, 6:131–145, 1987.

Chemical Abstracts, vol. 107, No. 13, Abstract No. 115934c., Japanese Patent 87 99,392 (May 8, 1987).

Chemical Abstracts, vol. 109, No. 23, Abstract No. 207, 900h, European Patent Application, EP 260, 032 (Mar. 16, 1988).

Chemical Abstracts, vol. 112, No. 7, Abstract No. 56,595w, Japanese Patent 89, 190,697 (Jan. 25, 1988).

Cancer Gene Therapy, vol. 1, No. 1, 1994 : pp. 65–71.

Uhlmann et al., Chemical Reviews, vol. 90, No. 4, pp. 544–584, (1990).

Mirabelli et al., Anti–Cancer Drug Design, vol. 6, pp. 647–661, (1991).

Fig. 1

PYRIMIDINE NUCLEOSIDE COMPOUNDS AND OLIGONUCLEOSIDE COMPOUNDS CONTAINING SAME

RELATED APPLICATIONS

This application is a continuation-in-part of patent application Ser. No. 08/003,487, filed Jan. 12, 1993 which is now abandoned, which is a continuation-in-part of parent application PCT/US91/00243, filed Jan. 11, 1991, which is a continuation-in-part of Ser. No. 07/463,358, filed Jan. 11, 1990, which is now abandoned.

FIELD OF THE INVENTION

This invention relates to the design and synthesis of certain 2- and 4-substituted pyrimidine nucleosides that are useful for incorporation into oligonucleotides. The oligonucleotides, in turn, are useful as diagnostic reagents, research reagents and in therapeutics.

BACKGROUND OF THE INVENTION

It is well known that most of the bodily states in multicellular organisms, including most disease states, are effected by proteins. Such proteins, either acting directly or through their enzymatic or other functions, contribute in major proportion to many diseases and regulatory functions in animals and man. Classical therapeutics has generally focused upon interactions with such proteins in efforts to moderate their disease-causing or disease-potentiating functions. In newer therapeutic approaches, modulation of the actual production of such proteins is desired. By interfering with the production of proteins, the maximum therapeutic effect might be obtained with minimal side effects. It is the general object of such therapeutic approaches to interfere with or otherwise modulate gene expression which would lead to undesired protein formation.

One method for inhibiting specific gene expression is with the use of oligonucleotides. Oligonucleotides complementary to a specific target messenger RNA (mRNA) sequence are used. Several oligonucleotides are currently undergoing clinical trials for such use.

Transcription factors interact with double-stranded DNA during regulation of transcription. Oligonucleotides can serve as competitive inhibitors of transcription factors to modulate the action of transcription factors. Several recent reports describe such interactions (see, Bielinska, et. al., *Science* 1990, 250, 997–1000; and Wu, et al., *Gene* 1990, 89, 203–209.)

Oligonucleotides also have found use in diagnostic tests. Such diagnostic tests can be performed using biological fluids, tissues, intact cells or isolated cellular components. As with the above gene expression inhibition, diagnostic use can take advantage of an oligonucleotides ability to hybridize with a complementary strand of nucleic acid. Hybridization is the sequence specific hydrogen bonding of oligonucleotides via Watson-Crick and/or Hoogsteen base pairs to RNA or DNA. The bases of such base pairs are said to be complementary to one another.

Oligonucleotides are also widely used as research reagents. They are useful for understanding the function of many other biological molecules as well as in the preparation of such other biological molecules. One particular use, the use of oligonucleotides as primers in the reactions associated with polymerase chain reaction (PCR), has been the cornerstone for the establishment of an ever expanding commercial business. The use of such PCR reactions has seemingly "exploded" as more and more use of this very important biological tool are practiced. The uses of PCR have extended into many areas in addition to those contemplated by its nobel laureate inventor. Examples of such new areas include forensics, paleontology, evolutionary studies and genetic counseling to name just a few. Primers are needed for each of these uses. Oligonucleotides, both natural and synthetic, serve as the primers.

Oligonucleotides also are used in other laboratory procedures. A number of these uses are described in common laboratory manuals such as *Molecular Cloning, A Laboratory Manual*, Second Ed., J. Sambrook, et al., Eds., Cold Spring Harbor Laboratory Press, 1989; and *Current Protocols In Molecular Biology*, F. M. Ausubel, et. al., Eds., Current Publications, 1993. Such uses include Synthetic Oligonucleotide Probes, Screening Expression Libraries with Antibodies and Oligonucleotides, DNA Sequencing, In Vitro Amplification of DNA by the Polymerase Chain Reaction and Site-directed Mutagenesis of Cloned DNA from Book 2 of *Molecular Cloning, A Laboratory Manual*, ibid. and DNA-Protein Interactions and The Polymerase Chain Reaction from Vol. 2 of *Current Protocols In Molecular Biology*, ibid.

To supply the users of oligonucleotides, many scientific journals now contain advertisements for either oligonucleotide precursors or for custom-synthesized oligonucleotides. This has become an important commercial use of oligonucleotides. Other oligonucleotides can be synthesized to have properties that are tailored for the desired use. Thus, a number of chemical modifications have been introduced into oligonucleotides to increase their usefulness in diagnostics, as research reagents, and as therapeutic entities. These modifications are designed to increase binding to a target strand, to assist in identification of the oligonucleotide or an oligonucleotide-target complex, to increase cell penetration, to provide stability against nucleases and other enzymes that degrade or interfere with the structure or activity of the oligonucleotides, to provide a mode of disruption (terminating event) once sequence-specifically bound to a target, or to improve the pharmacokinetic properties of the oligonucleotides.

To serve some of the above-noted uses, reactive functionalities can be tethered to an oligonucleotide and directed at phosphodiester and heterocyclic centers in target compounds. The positioning of these functionalities may require the synthesis of C-2 and C-4 substituted pyrimidine nucleosides with the following general features: (a) preservation of Watson-Crick hybridization characteristics; (b) stability during automated DNA synthesis; and (c) the conformational rigidity of a carbon tether to accurately place functionalities near their target. Criteria (a) and (b) are not met by readily available 2-O-, 2-S-, or 2-N-alkyl pyrimidine nucleosides since these groups are sensitive to nucleophilic displacement. For example, deprotecting DNA oligomers containing S-alkylated moieties with concentrated ammonia likely would yield displacement products at C-2 and C-4 pyrimidine positions. In addition, 2-O-, 2-S-, and 2-N-alkyl groups would preclude the availability of an imino proton at N-3, which is necessary for hydrogen bonding. Likewise, nucleosides having 2-N-alkyl groups at these positions would fail to meet criteria (b) and (c) due to their chemical instability and the spatial instability inherent in an inversion of configuration of a tertiary nitrogen. Accordingly, there remains a need in the art for novel 2- and 4-substituted pyrimidines that meet the design criteria set forth above.

OBJECTS OF THE INVENTION

It is one object of this invention to provide oligonucleotides for use in diagnostics, therapeutics and as research reagents.

It is another object of this invention to provide oligonucleotides that effectively modulate the activity of RNA or DNA or proteins.

It is a further object to provide novel 2-substituted pyrimidines.

These and other objects will become apparent to persons of ordinary skill in the art from a review of the present specification and appended claims.

SUMMARY OF THE INVENTION

In accordance with these and other objects, the present invention provides novel C-2 and C-4 modified pyrimidine nucleosides and oligonucleosides. In certain embodiments, the compounds of the invention have structure 1 or structure 2:

1

2 wherein:

J is N or CH;

$R_5$ is H or $CH_3$;

one of $R_2$ and $R_4$ is =O, =NH, or =$NH_2^+$ or the tautomeric form —OH, —$NH_2$, —$NH_3^+$; and the other of $R_2$ and $R_4$ is Q, =C($R_A$)—Q, C($R_A$)($R_B$)—C ($R_C$) ($R_D$)—Q, C($R_A$)=C ($R_C$)—Q or C≡C—Q;

$R_A$, $R_B$, $R_C$ and $R_D$ independently are H, SH, OH, $NH_2$, or $C_1$–$C_{20}$ alkyl, or one of ($R_A$)($R_B$) or ($R_C$)($R_D$) is =O;

Q is halogen, hydrogen, $C_1$–$C_{20}$ alkyl, $C_1$–$C_{20}$ alkylamine, $C_1$–$C_{20}$ alkyl-N-phthalimide, $C_1$–$C_{20}$ alkylimidazole, $C_1$–$C_{20}$ alkylbis-imidazole, imidazole, bis-imidazole, amine, N-phthalimide, $C_2$–$C_{20}$ alkenyl, $C_2$–$C_{20}$ alkynyl, hydroxyl, thiol, keto, carboxyl, nitrates, nitro, nitroso, nitrile, trifluoromethyl, trifluoromethoxy, O-alkyl, S-alkyl, NH-alkyl, N-dialkyl, O-aralkyl, S-aralkyl, NH-aralkyl, azido, hydrazino, hydroxylamino, isocyanato, sulfoxide, sulfone, sulfide, disulfide, silyl, O-(hydroxyl protecting group), a leaving group, a heterocycle, an intercalator, a reporter molecule, a conjugate, a polyamine, a polyamide, a polyethylene glycol, a polyether, a group that enhances the pharmacodynamic properties of oligonucleotides, a group that enhances the pharmacokinetic properties of oligonucleotides, a RNA cleaving moiety or a depurination enhancing group;

$T_3$ and $T_5$ independently are H, phosphate, an activated phosphate, a hydroxyl protecting group, a nucleoside, a nucleotide, an oligonucleotide or an oligonucleoside;

$X_1$ and $X_2$ independently are hydrogen, halogen, hydroxyl, O-(hydroxyl protecting group), thiol, carboxyl, nitrate, nitro, nitroso, nitrile, trifluoromethyl, trifluoromethoxy, O-alkyl, S-alkyl, NH-alkyl, N-dialkyl, O-aralkyl, S-aralkyl, NH-aralkyl, amino, azido, hydrazino, hydroxylamino, isocyanato, sulfoxide, sulfone, sulfide, disulfide, silyl, heterocyclic, alicyclic, carbocyclic, intercalators, reporter molecules, conjugates, polyamines, polyamides, polyethylene glycols, polyethers, groups that enhance the pharmacodynamic properties of oligonucleotides, or groups that enhance the pharmacokinetic properties of oligonucleotides.

For structure 1, when $T_5$ is a hydroxyl protecting group or together $T_3$ and one of $X_1$ or $X_2$ is a hydroxyl protecting group, then $R_2$ should not be $CH_3$; when $T_3$ and $T_5$ are H or O-benzoyl, then $R_2$ should not be $CH_2OC_6H_5$; and when $R_4$ is Q then Q is not hydroxyl, thiol, amino or hydrogen.

The present invention also provides methods for preparing the compounds of the invention and synthetic intermediates employed in the methods. In certain embodiments, the methods involve reacting 2,2'- or 2,5'-anhydropyrimidines with a nucleophile to effect attack of the nucleophile at the 2-pyrimidine position. The nucleophile can have general formula $R_2$ or can be a functional group that can be modified to have formula $R_2$. In further embodiments, the methods involve reacting 4-halopyrimidines with substituted alkynes in the presence of an organometallic coupling reagent for a time and under reaction conditions effective to form a covalent bond between the alkyne and the pyrimidine 4-position.

The invention also provides methods for modulating the production or activity of a protein in an organism comprising contacting the organism with a compound according to the invention. It is preferred that the compound include a base sequence that is complementary to a RNA or DNA sequence that codes for the protein. This "targeting portion" of the compound is, thus selected to be complementary to the targeted portion of DNA or RNA such that the compound can bind to the target portion.

DETAILED DESCRIPTION OF INVENTION

In a general sense, the present invention is directed to nucleosides that include 2- and 4-modified pyrimidine bases, and to more complex compounds that include the nucleosides. The term "nucleoside" as used in connection with this invention refers to a unit made up of a heterocyclic base and its sugar. The term "nucleotide" refers to a nucleoside having a phosphate group on its 3' or 5' sugar hydroxyl group. Thus, nucleosides, unlike nucleotides, have no phosphate group. "Oligonucleotide" refers to a plurality of joined nucleotide units formed in a specific sequence from naturally occurring bases and pentofuranosyl groups joined through a sugar group by native phosphodiester bonds. This term refers to both naturally occurring and synthetic species formed from naturally occurring subunits.

The compounds of the invention generally can be viewed as "oligonucleotide analogs", that is, compounds which function like oligonucleotides but which have non-naturally occurring portions. Oligonucleotide analogs can have altered sugar moieties, altered base moieties or altered inter-sugar linkages. For the purposes of this invention, an oligonucleotide analog having non-phosphodiester bonds, i.e., an altered inter-sugar linkage, is considered to be an "oligonucleoside." The term "oligonucleoside" thus refers to a plurality of nucleoside units joined by linking groups other than native phosphodiester linking groups. The term "oligomers" is intended to encompass oligonucleotides, oligonucleotide analogs or oligonucleosides. Thus, in speaking of "oligomers" reference is made to a series of nucleosides or nucleoside analogs that are joined via either naturally occurring phosphodiester bonds or other, non-naturally occurring linkages.

The oligonucleosides of the invention preferably comprise from about 5 to about 50 nucleosides, each nucleoside having the same or different structure. The targeting portions of the oligonucleosides preferably comprise about 8 to about 40 base nucleosides, more preferably about 12 to 20 base nucleosides.

It is preferred that an oligonucleoside of the invention include at least one 2- or 4-modified pyrimidine at its 3'- or 5'-terminus. In certain embodiments, the oligonucleoside has 1–3 modified pyrimidines at its 3'-terminus.

The nucleosides of the invention can be linked with one another or with other nucleosides or oligonucleosides via a sugar linking group. The linking groups can be any structure capable of linking sugar moieties of oligonucleosides to form the targeting portion of the compositions of this invention. It is preferred that these sugar linking groups comprise phosphodiester groups or derivatives thereof. Derivatives of the phosphodiester structure can include substitution of a sulphur, methyl, methyl oxide, or amine group for an oxygen. The sugar phosphate nucleic acid backbone may be modified as a phosphorothioate, methylphosphonate, or phosphate alkylated moiety. The phosphodiester linkage may also be replaced by a carbon or ether linkage.

In certain embodiments, the 2-substituted pyrimidine compounds of the invention are represented by the structures 1 and 2:

1

2 wherein
J is N or CH;
$R_5$ is H or $CH_3$;
one of $R_2$ and $R_4$ is =O, =NH, or =$NH_2^+$ or the tautomeric form —OH, —$NH_2$, —$NH_3^+$; and the other of $R_2$ and $R_4$ is Q, =C($R_A$)—Q, C($R_A$)($R_B$)—C($R_C$)($R_D$)—Q, C($R_A$)=C($R_C$)—Q or C≡C—Q;
$R_A$, $R_B$, $R_C$ and $R_D$ independently are H, SH, OH, $NH_2$, or $C_1$–$C_{20}$ alkyl, or one of ($R_A$)($R_B$) or ($R_C$)($R_D$) is =O;
Q is halogen, hydrogen, $C_1$–$C_{20}$ alkyl, $C_1$–$C_{20}$ alkylamine, $C_1$–$C_{20}$ alkyl-N-phthalimide, $C_1$–$C_{20}$ alkylimidazole, $C_1$–$C_{20}$ alkylbis-imidazole, imidazole, bis-imidazole, amine, N-phthalimide, $C_2$–$C_{20}$ alkenyl, $C_2$–$C_{20}$ alkynyl, hydroxyl, thiol, keto, carboxyl, nitrates, nitro, nitroso, nitrile, trifluoromethyl, trifluoromethoxy, O-alkyl, S-alkyl, NH-alkyl, N-dialkyl, O-aralkyl, S-aralkyl, NH-aralkyl, azido, hydrazino, hydroxylamino, isocyanato, sulfoxide, sulfone, sulfide, disulfide, silyl, O-(hydroxyl protecting group), a leaving group, a heterocycle, an intercalator, a reporter molecule, a conjugate, a polyamine, a polyamide, a polyethylene glycol, a polyether, a group that enhances the pharmacodynamic properties of oligonucleotides, a group that enhances the pharmacokinetic properties of oligonucleotides, a RNA cleaving moiety or a depurination enhancing group;
$T_3$ and $T_5$ independently are H, phosphate, an activated phosphate, a hydroxyl protecting group, a nucleoside, a nucleotide, an oligonucleotide or an oligonucleoside;
$X_1$ and $X_2$ independently are hydrogen, halogen, hydroxyl, O-(hydroxyl protecting group), thiol, carboxyl, nitrate, nitro, nitroso, nitrile, trifluoromethyl, trifluoromethoxy, O-alkyl, S-alkyl, NH-alkyl, N-dialkyl, O-aralkyl, S-aralkyl, NH-aralkyl, amino, azido, hydrazino, hydroxylamino, isocyanato, sulfoxide, sulfone, sulfide, disulfide, silyl, heterocyclic, alicyclic, carbocyclic, intercalators, reporter molecules, conjugates, polyamines, polyamides, polyethylene glycols, polyethers, groups that enhance the pharmacodynamic properties of oligonucleotides, or groups that enhance the pharmacokinetic properties of oligonucleotides.

For structure 1, when $T_5$ is a hydroxyl protecting group or together $T_3$ and one of $X_1$ or $X_2$ is a hydroxyl protecting group, then $R_2$ should not be $CH_3$; when $T_3$ and $T_5$ are OH or O-benzoyl, then $R_2$ should not be $CH_2OC_6H_5$.

Preferred $R_2$ and $R_4$ groups include C($R_A$)=C($R_C$)—Q, preferably where $R_A$ is OH, SH or $NH_2$ and $R_C$ is H, more preferably where Q is $C_{1-20}$ or $C_{1-6}$ alkyl; and C($R_A$)($R_B$)—C($R_C$)($R_D$)—Q, preferably where $R_A$ and $R_B$ are both hydrogen and $R_C$ and $R_D$ together are =O.

Preferred structures are also those in which one of $X_1$ or $X_2$ is hydrogen and the other is hydroxyl, or where both are hydrogen; where $R_4$ is =O; where $R_5$ is hydrogen or $CH_3$; or where $T_3$ is an activated phosphate and $T_5$ is a hydroxyl protecting group; or where one of $T_3$ or $T_5$ is an oligonucleotide or an oligonucleoside, or both are H.

A wide variety of protecting groups can be employed in the methods of the invention. See, e.g., Beaucage, et al., *Tetrahedron* 1992, 12, 2223. In general, protecting groups render chemical functionality inert to specific reaction conditions, and can be appended to and removed from such functionality in a molecule without substantially damaging the remainder of the molecule. Representative hydroxyl protecting groups include t-butyldimethylsilyl (TBDMS), t-butyldiphenylsilyl (TBDPS), dimethoxytrityl (DMTr), monomethoxytrityl (MMTr), and other hydroxyl protecting groups as outlined in the above-noted Beaucage reference.

Leaving groups according to the invention are chemical functional groups that can be displaced from carbon atoms by nucleophilic substitution. Representative leaving groups include but are not limited to halogen, alkylsulfonyl, substituted alkylsulfonyl, arylsulfonyl, substituted arylsulfonyl, hetercyclcosulfonyl or trichloroacetimidate groups. Preferred leaving groups include chloro, fluoro, bromo, iodo, p-(2,4-dinitroanilino)benzenesulfonyl, benzenesulfonyl, methylsulfonyl (mesylate), p-methylbenzenesulfonyl (tosylate), p-bromobenzenesulfonyl, trifluoromethylsulfonyl (triflate), trichloroacetimidate, acyloxy, 2,2,2-trifluoroethanesulfonyl, imidazolesulfonyl, and 2,4,6-trichlorophenyl groups.

Heterocycles according to the invention are functional groups that include atoms other than carbon in their cyclic backbone.

Intercalators according to the invention generally include non-carcinogenic, polycyclic aromatic hydrocarbons or heterocyclic moieties capable of intercalating between base pairs formed by a hybrid oligonucleotide/RNA target sequence duplex. Intercalators can include naphthalene, anthracene, phenanthrene, benzonaphthalene, fluorene, carbazole, acridine, pyrene, anthraquinone, quinoline, phenylquinoline, xanthene or 2,7-diazaanthracene groups. Other intercalators believed to be useful are described by Denny, *Anti-Cancer Drug Design* 1989, 4, 241. Another intercalator is the ligand 6-[[[9-[[6-(4-nitrobenzamido) hexyl]amino]acridin-4-yl]carbonyl]-amino] hexanoylpentafluorophenyl ester.

Reporter molecules are those compounds that have physical or chemical properties that allow them to be identified in gels, fluids, whole cellular systems, broken cellular systems and the like utilizing physical properties such as spectroscopy, radioactivity, colorimetric assays, fluorescence, and specific binding. Particularly useful reporter molecules include biotin and fluorescein dyes. Particularly useful as reporter molecules are biotin, fluorescein dyes, alkaline phosphates, and horseradish peroxidase.

The term "depurination enhancing moiety" includes chemical moieties that are capable of enhancing the rate of depurination of a purine-containing nucleic acid species. Depurination enhancing moieties enhance the rate of removal, break down, and/or loss of adenine and guanine nucleobases from adenosine and guanosine nucleotides. They also enhance the rate of the removal, break down, and/or loss of other purine-containing nucleotides such as 7-methylguanosine, 3-methylguanosine, wyosine, inosine, 2-aminoadenosine, and other "minor" or synthetic nucleotides. Preferred depurination enhancing moieties are sulfur-containing compounds, including sulfur-containing heterocycles and both cyclic and alicyclic sulfonium compounds. Specific examples include but are not limited to thiophene, thianthrene, isothiazole, alkyl sulfonium salts, thiophenium salts, 1,3-thiazolium salts, 1,2-oxathiolanium salts, alkyl 1,4-dithianium salts, alkyl thiazolium salts, thioniabicyclo [2,2,1]heptane salts and 3aH-1,6-dithia-6a-thioniapentalene salts. Anions for such salts include halide anions and other anions.

Conjugates are functional groups that improve the uptake of the compounds of the invention. Representative conjugates include steroid molecules, reporter molecules, non-aromatic lipophilic molecules, reporter enzymes, peptides, proteins, water soluble vitamins, and lipid soluble vitamins, as disclosed by U.S. patent application Ser. No. 782,374, filed Oct. 24, 1991, and PCT Application US92/09196, filed Oct. 23, 1992, the disclosures of which are incorporated herein by reference. Representative conjugates also are disclosed by Goodchild, *Bioconjugate Chemistry* 1990, 1, 165.

Activated phosphates according to the invention are disclosed by Beaucage, et al., *Tetrahedron* 1982, 2223.

As will be recognized by those of ordinary skill in the art, the base portion of structure 1 can be equivalently represented by its tautomeric forms. Thus, the recitation of structure 1 in connection with the present invention is intended to include each of the following tautomeric structures:

There appear to have been few reported syntheses of 2-alkyl substituted pyrimidine nucleosides. Witkop, et al., *J. Amer. Chem. Soc.* 1969, 91, 7751 reported that treatment of a protected 2,5'-anhydrouridine with dimethylsulfoxonium methylid (DMSY) gave a 2-methylpyrimidin-4-one riboside after hydrogenolysis of the sulfoxonium group. 2-Methyl-pyrimidin-4-one ribonucleosides were also obtained when Rosenthal, et al., *Carbohydr. Res.* 1980, 78, 33, examined the reaction of 2,2'-anhydrouridines with 1,3-dithiane/n-butyllithium followed by desulfurization. Vorbrüggen, et al., *Angew. Chem. Int. Ed.* 1976, 15, 689, have investigated the Eschenmoser sulfide extraction of 2- and 4-S-phenacylated-2-thiouridines to yield 2- and 4-phenacetylpyrimidin-4-one ribonucleosides. However, these methods presented a number of problems. For example, attempts to synthesize the target nucleosides by DMSY chemistry according to Witkop's work resulted in laborious purifications and low yields. The Eschenmoser sulfide contraction is limited by the stability and limited availability of functionalized α-haloketones.

In certain embodiments, 2-substituted pyrimidine nucleosides of the invention are synthesized by nucleophilic substitution of 2,2'- or 2,5'-anhydropyrimidines. One preferred reaction sequence is shown in Scheme 1.

Scheme 1

At room temperature, the reaction of the lithium enolates of acetone, methylethylketone, 2-pentanone or 2-hexanone with a 3'-O-t-butyldiphenylsilyl-2,5'-anhydrothymidine 5 ($T_3$=TBDMS, $X_1$=H, $R_5$=$CH_3$ or H) yields the corresponding 2-(β-ketoalkyl)-pyrimidin-4-one deoxynucleosides 6a–d ($X_1$=H; $T_5$=H; $R_2$=═CHC(O)$CH_3$ (6a), ═CHC(O)$CH_2CH_3$ (6b), ═CHC(O)($CH_2$)$_2CH_3$ (6c), ═CHC(O)($CH_2$)$_3CH_3$ (6d)) following removal of the protecting groups. Likewise, reaction of the lithium enolate of hexanone with a protected 2-5'-anhydrouridine 7 ($T_3$=TBDMS, $X_1$=OTBDMS, $R_5$=$CH_3$ or H) yields the corresponding 2-(2-hexanon-1-yl)pyrimidin-4-one ribonucleoside 8 ($X_1$= ribo OH, $T_5$=$T_3$=H, $R_5$=$CH_3$ or H, $R_2$=═CHC(O)($CH_2$)$_3CH_3$). The nucleoside structures 6a–d and 8 were isolated as yellowish oils with characteristic ultraviolet maxima near 320 nm; nucleoside structures 6a–d were found to be unstable. The downfield shift of the amidine/enol signal in the $^1$H-NMR spectra of these compounds is indicative of protons bound by N-3 and keto oxygen. Further, two tautomeric structures can be drawn which account for the vinylic character of the alpha proton of the tether. 3',5'-(di-O-MMTr, -DMTr, -TBDMS or -TBDPS)-2,2'-anhydrouridines 9 ($T_3$=$T_5$=MMTr, DMTr, TBDMS, TBDPS) can be used to synthesize the corresponding arabinosides. The reaction of structure 9 ($T_3$=$T_5$= TBDMS) with the lithium enolate of 2-hexanone followed by a deprotection of the intermediate produced the 2-(2-hexanon-1-yl)pyrimidin-4-one arabinonucleoside structure 10 ($X_1$=ara OH, $T_3$=$T_5$=H, $R_5$=$CH_3$ or OH, $R_2$=═CHC(O)($CH_2$)$_3CH_3$) in good yield. Also, it has been found that reaction of structure 9 ($T_3$=$T_5$=TBDMS) with the lithium enolate of 2-pentanone under standard conditions yields the protected 2-alkylated arabinonucleoside 11 ($X_1$=ara OH, $T_3$=$T_5$=H, $R_5$=$CH_3$ or H, $R_2$=═CHC(O)($CH_2$)$_2CH_3$) in 75% yield.

Figure 1:
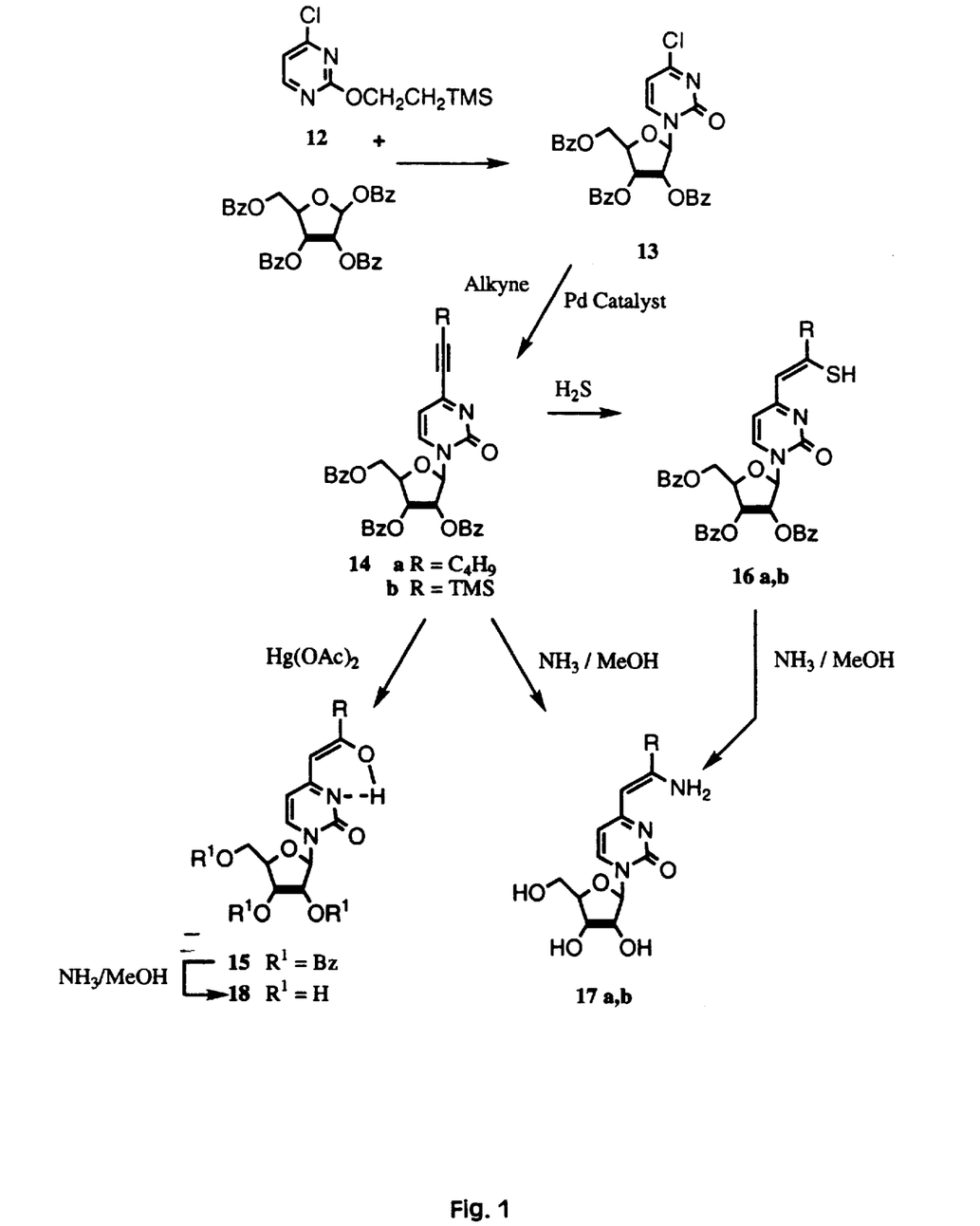
FIG. 1 shows certain synthetic methods according to the present invention.

The 4-substituted pyrimidine compounds of the invention are synthesized by metal-mediated coupling 2-halopyrimidines and substituted alkynes. One preferred procedure is shown in FIG. 1. In this approach, terminal alkynes are coupled to a 4-chloropyrimidine ribonucleoside by methods generally in accordance with Heck, "Palladium Reagents in Organic Synthesis" Academic Press, Orlando, Fla. (1985). A 4-chloro-2-trimethylsilylethoxy-pyrimidine, structure 12, can be prepared by reaction of trimethylsilyethanol/n-butyllithium and 2,4-dichloropyrimidine in tetrahydrofuran (THF) at −20° C. Condensation of structure 12 and 1-O-acetyl-2,3,5-tri-O-benzoyl-β-D-ribofuranose is carried out using TMS-triflate/$CH_3CN$ generally according to the procedures of Vorbruggen, et al., Chem. Ber. 1981, 114, 1234. Coupling of the 4-chloro-1-(2,3,5-tri-O-benzoyl-β-D-ribofuranosyl) pyrimidin-2-one, structure 13, with an alkyne, such as 1-hexyne, and catalyzed by bis-triphenylphosphine palladium (II) dichloride/copper (I) iodide provides 4-(1-hexyn-1-yl)pyrimidin-2-one ribonucleoside, structure 14a (R=$C_4H_9$). Similarly, the reaction of structure 13 with trimethylsilylacetylene provides 4-trimethylsilylethynylpyrimidin-2-one ribonucleoside, structure 14b (R=TMS).

Conjugated alkyne nucleoside structures 14a,b can be reacted with $H_2S$ to yield 4-(2-thiol-1-alken-1-yl)pyrimidin-2-one ribonucleoside structures 16a (R=$C_4H_9$) and 16b (R=TMS), or with methanolic ammonia to yield deprotected 4-(2-amino-1-alken-1-yl)pyrimidin-2-one riboside structures 17a (R=$C_4H_9$) and 17b (R=TMS). Interestingly, the reaction of the 4-(2-thiol-1-hexen-1-yl)pyrimidin-2-one, 16, with ammonia displaces the thiol group and produces the enamine structure 17a, identical to the product obtained from the reaction of alkyne 14a with ammonia. Hydration of structure 14a followed by deprotection of intermediate structure 15a ($R_1$=benzoyl) yields the enolized 4-(2-hydroxy-1-hexen-1-yl)pyrimidin-2-one ribonucleoside, structure 18a ($R_1$=H).

The enol nature of the 2-(β-ketoalkyl)- and 4-(β-ketoalkyl)pyrimidinone nucleoside analogs (6a–d, 8, 10, 11 and 18a) offer the potential for Watson-Crick hybridization. Because of this potential they can be considered as analogues of thymidine and cytidine. Thus hybridization of these compounds to adenosine and guanosine in a bifurcated bonding scheme is possible.

The compounds of this invention can be used in diagnostics, therapeutics, and as research reagents and kits. In certain uses in diagnostics and as research reagents, the pyrimidine nucleosides of the invention are converted to their corresponding phosphoramidate nucleotide and incorporated into oligonucleotides. For incorporation into oligonucleotides, they can be used in place of a standard or normal nucleotide to alter the properties of the diagnostic oligonucleotide reagent, as for instance, to increase the nuclease resistances of the oligonucleotide or to modulate (i.e., increase or decrease) hybridization of the oligonucleotide to a target.

Oligonucleotides that incorporate the compounds of the invention can be used for the selective binding of RNA for other research and diagnostic purposes. Such selective, strong binding is accomplished through interaction of RNA or DNA with compounds of the invention that are resistant to degradative nucleases and which hybridize more strongly and with greater fidelity than known oligonucleotides or oligonucleotide analogs.

For certain uses of the compounds of the invention, be it diagnostic use or therapeutic use, it is preferred that a target RNA or DNA be preselected to comprise that portion of DNA or RNA which codes for a protein whose formation or activity is to be modulated. The targeting portion of the compound to be employed is, thus, selected to be complementary to the targeted portion of DNA or RNA.

In accordance with a further preferred embodiment, the compounds of the invention mimic the secondary structure of natural nucleic acid structures that bind to particular proteins. The nucleic acid mimic can then be used for isolation and identification of the protein structure or for competitive binding to the protein structure. One such nucleic acid structure is the TAR structure, which binds the tat protein. By effectively mimicking TAR, compounds according to the invention bind the tat protein and thereby form a complex that can be isolated and identified using affinity chromatography.

For therapeutic use, oligonucleotide analogs are administered to animal suffering from a disease modulated by some protein. It is preferred to administer to patients suspected of suffering from such a disease an amount of oligonucleotide analog that is effective to reduce the symptomology of that disease. One skilled in the art can determine optimum dosages and treatment schedules for such treatment regimens.

In accordance with preferred embodiments, compounds of the invention hybridize to the mRNA of various pathogenic organisms. Preferred compounds for such use include those incorporating a complementary sequences for herpes, papilloma and other viruses.

It is generally preferred to administer the therapeutic agents in accordance with this invention internally such as orally, intravenously, or intramuscularly. Other forms of administration, such as transdermally, topically, or intralesionally may also be useful. Inclusion in suppositories may also be useful. Use of pharmacologically acceptable carriers is also preferred for some embodiments.

Additional objects, advantages, and novel features of this invention will become apparent to those skilled in the art upon examination of the following examples thereof, which are not intended to be limiting, wherein parts and percents are by weight unless otherwise indicated.

EXAMPLE 1

4-Chloro-2-trimethylsilylethoxy-pyrimidine, 12

A solution of trimethylsilylethanol (10 g, 85 mmol) in 30 mL anhydrous THF was cooled to −68° C. in a dry ice/isopropanol bath. A solution of n-butyl lithium (33.8 mL, 2.5M in THF) was added dropwise over 15 min. The solution was stirred for 10 min at this temperature and then added to a solution of 2,4-dichloropyrimidine (12.62 g. 85 mmol) in 75 mL THF at −35 to −25° C. The final yellowish solution was allowed to come to room temperature under an argon atmosphere then stirred at this temperature for 1 hr. This solution was diluted with 200 mL of diethylether and washed with cold water (100 mL), saturated NaHCO$_3$ (100 mL) and brine, then dried over MgSO$_4$, filtered and evaporated to yield a tan syrup. This syrup may be crystallized from hexanes at −60° C. to yield 12 as a light yellow solid, 17.8 g (91%). $^1$H-NMR (CDCl$_3$): δ 8.36 (d, 1 H, H-6); 6.93 (d, 1 H, 5-H); 4.43 and 1.17 (t,t; 4 H; CH$_2$CH$_2$) 1.06 (bs, 9 H. TMS).

EXAMPLE 2

4-Chloro-1-(2,3,5-tri-O-benzoyl-β-D-ribofuranosyl)pyrimidin-2-one, 13

A solution of 12 (8.17 g. 35.4 mmol) in 200 mL anhydrous acetonitrile is treated with 1-O-acetyl-2,3,5-tri-O-benzoyl-D-ribofuranose (Pfanstiehl) at room temperature and under an atmosphere of argon. To this mixture is added TMS-triflate (6.11 mL, 35.4 mmol) and the mixture stirred at this temperature for 2 hr. Evaporation of the solvents in vacuo yielded an amber syrup which was immediately redissolved in 300 mL CH$_2$Cl$_2$, washed with cold, saturated NaHCO$_3$ (2×150 mL), dried over magnesium sulfate, filtered and evaporated to a tan residue. Trituration of this residue with cold, anhydrous acetonitrile yielded analytically pure 13, 14.4 g (71%). $^1$H-NMR (DMSO-d$_6$): δ 8.39 (d, 1 H, 6-H, J$_{6,5}$=11.8 Hz); 8.0–7.4 (m, 15 H, aromatic); 6.68 (d, 1 H, H-5); 6.11 (d, 1H, H-1', J1,2=2 Hz); 5.95 (m, 2 H, H-2',3'); 4.85 (m, 1 H, H-4'); 4.70 (m, 2 H, H-5',5"). Anal. Calcd for C$_{30}$H$_{23}$N$_2$O$_8$Cl: C, 62.67; H, 4.03; N, 4.87. Found: C, 62.21; H, 3.92; N, 4.80.

EXAMPLE 3

4-(1-Hexyn-1-yl)-1-(2,3,5-tri-O-benzoyl-β-D-ribofuranosyl)-pyrimidin-2-one, 14a

A suspension of bis-triphenylphosphine palladium (II) dichloride (0.35 g, 0.5 mmol) and copper (I) iodide (95 mg, 0.5 mmol) in THF (45 mL, distilled from Na-benzophenone ketyl) is sparged with dry argon gas for 10 min. To this suspension is added 1-hexyne (2.46 g, 30 mmol) followed by triethylamine (5 mL). The suspension is stirred at room temperature under argon for 15 min. A similarly sparged solution of the 2-chloro-1-(2,3,5-tri-O-benzoyl-b-D-ribofuranosyl)pyrimidin-4-one (13, 5.75 g, 10 mmol) in THF (15 mL) is added to the suspension of catalyst and the mixture stirred for 1 hr. The dark mixture is filtered through Celite and the filtrate evaporated in vacuo to afford a dark syrup. This syrup was triturated with cold diethylether, filtered and then dissolved in dichloromethane.

The solution is washed with cold 1N HCl, dried over magnesium sulfate and again evaporated in vacuo. The resulting residue was triturated with methanol to yield 14a as a white solid, 5.5 g, 88%. $^1$H-NMR (DMSO-d$_6$): δ 8.33 (d, 1 H, H-6, J$_{6,5}$=7 Hz); 8.1–7.4 (m, 15 H, aromatic); 6.53 (d, 1 H, H-5); 6.24 (s, 1 H, H-1'); 2.52, 1.50 and 0.94 (3 m, 9 H, n-butyl). Anal. Calcd for C$_{36}$H$_{32}$N$_2$O$_8$: C, 69.67; H, 5.19; N, 4.51. Found: C, 69.32; H, 5.13; N, 4.44.

EXAMPLE 4

2-(2-Trimethylsilylethynyl)1-(2,3,5-tri-O-benzoyl-β-D-ribofuranosyl)pyrimidin-2-one, 14b Coupling of chloro nucleoside 13 ( 5.74 g, 10 mmol) with trimethylsilyl acetylene (4.9 g, 50 mmol) according to the procedure described above gave 14b as a white amorphous solid, 5.12 g (80%). $^1$H-NMR (DMSO-d$_6$): 8.37 (d, 1 H, H-6, J$_{6,5}$=6.5 Hz); 8.1–7.4 (m, 15 H, aromatic); 6.60 (d, 1 H, H-5); 6.22 (s, 1 H, H-1'); 0.29 (s, 9 H, TMS). Anal. Calcd for C$_{32}$H$_{32}$N$_2$O$_8$Si: C, 66.02; H, 5.06; N, 4.40. Found: C, 65.68; H, 4.93; N, 4.39.

EXAMPLE 5

4-(2-Hexanon-1-yl)-1-(2,3,5-tri-O-benzoyl-β-D-ribofuranosyl)-pyrimidin-2-one, 15a A solution of 14a (0.77 g, 1.2 mmol) in 50 mL acetone is treated with a 0.1M solution of Hg(OAc)$_2$ (15 mL) in aqueous acetic-H$_2$O (1:1) and the mixture stirred at room temperature for 18 hr. The reaction is further diluted with dichloromethane (100 mL), washed with cold saturated NaHCO$_3$ solution, dried over magnesium sulfate and evaporated in vacuo. The resulting residue is flash-chromatographed using chloroform/acetone 19:1 to afford a yellowish solid. This solid is triturated with cold methanol to afford 15a, 0.47 g, 59%. $^1$H-NMR (DMSO-d6): 12.5 (s, 1 H, enol); 8.0–7.4 (m, 16 H, H-6 plus aromatic); 6.15 (d, 1 H, H-1', J=2 Hz); 5.90 (m, 3 H, H-5, 2',3'); 5.39 (s, 1 H, vinylic, $J_{vinyl,\ allyl}$=<1 Hz)); 2.30, 1.47, 1.24 and 0.86 (4 m, 9 H, n-butyl). Anal. Calcd for $C_{36}H_{34}N_2O_9$: C, 67.70; H, 5.37; N, 4.39. Found: C, 67.51; H, 5.28; N, 4.28.

EXAMPLE 6

4-(2-Thiol-1-hexen-1-yl)-1-(2,3,5-tri-O-benzoyl-β-D-ribofuranosyl)pyrimidin-2-one, 16a A solution of compound 14a (0.64 g) in THF is sparged with a steady stream of $H_2S$ gas for 3 min. The solution is then evaporated in vacuo and flash chromatographed using $CHCl_3$/ethyl acetate (9:1) to afford 16a as an amber foam, 0.25 g (37%). $^1$H-NMR (DMSO-d6): δ 15.3 (s, 1H, thiol); 6.43 (s, 1 H, vinylic, $J_{vinyl,\ allyl}$<1 Hz); 6.23 (m, 2 H, H-1' and H-5); 2.7, 1.8, 1.3 and 0.9 (4 m, 9 H, n-butyl). Anal. Calcd for $C_{36}H_{34}N_2O_8S$: C, 66.04; H, 5.23; N, 4.27; S, 4.89. Found: C, 66.10; H, 5.18; N, 4.13; S, 4.43.

EXAMPLE 7

4-(2-Amino-1-hexen-1-yl)-1-β-D-ribofuranosyl-pyrimidin-2-one, 17a

A solution of 14a (1.2 g, 1.9 mmol) in methanolic ammonia (saturated at −20° C.) was stirred in a pressure bottle for 18 hr. Evaporation of the solvents and flash chromatography of the residue using ethyl acetate/methanol (4:1) gave 17 a as a light yellow solid, 0.47 g (77%). $^1$H-NMR (DMSO-d$_6$): δ 10.2 and 7.7 (2 bs, 2 H, $NH_2$); 7.83 (d, 1 H, H-6, $J_{6,5}$=6.9 Hz); 5.78 (s, 1 H, H-1'); 4.72 (s, 1 H, vinylic); 2.17, 1.50, 1.30 and 0.90 (4 m, 9 H, n-butyl).

EXAMPLE 8

4-(2-Amino-1-ethen-1-yl)-1-β-D-ribofuranosyl-pyrimidin-2-one, 17b

A solution of 14b (1.2 g, 1.88 mmol) in 30 mL methanolic ammonia (saturated at −20° C.) was stirred at room temperature for 18 hr. The solvents were evaporated in vacuo to a bright red syrup. This syrup was triturated with diethyl-ether ($Et_2O$) (3×30 mL) then redissolved in methanol (MeOH) and reevaporated to give a solid orange foam. A portion of this foam was chromatographed on two preparative thin layer chromatography (TLC) plates using ethyl acetate/MeOH, 4:1 to give a sample for NMR. The purity of this sample was not sufficient to fit elemental analysis. $^1$H-NMR (DMSO-d6): δ 9.5 and 7.7 (2 bs, 2 H, $NH_2$); 7.92 (d, 1 H, H-6, $J_{6,5}$=7 Hz); 7.0 (m, d w/$D_2O$ exch., 1 H, H-(b-vinylic), $J_{b-a}$=7.4 Hz); 5.77 (s, 1 H, H-1'); 5.98 (d, 1 H, H-5); 4.74 (d, 1 H, H-(a-vinylic).

EXAMPLE 9

2-Thio-1-(3',5'-di-O-benzoyl-2'-O-methyl-β-D-ribofuranosyl)-pyrimidin-4-one

2-Thiouracil (1.282 g, 10 mmol), a few crystals of ammonium sulfate, a few drops of trimethylsilyl chloride and 1,1,1,3,3,3-hexamethyldisilazane (HMDS, 20 ml) were refluxed overnight. The clear, greenish solution was evaporated under the exclusion of moisture. A solution of 2-O-methyl-1,3,5-tri-O-benzoyl-α-D-ribose (4.76 g, 10 mmol) in acetonitrile (50 ml) was added to give a clear solution. $SnCl_4$ is added and the mixture became turbid and then immediately became clear thereafter. The mixture was stirred for three hours and then poured into a stirred mixture of saturated $NaHCO_3$ and dichloromethane (200/400 ml). The organic layer was separated, dried over $Na_2SO_4$, filtered and evaporated. The amorphous residue was crystallized from hot ethanol to yield colorless needles (1.895 g, 39%). $^1$H-NMR ($CDCl_3$): δ 10.3 (s, 1 H, NH); 7.8 (d, 1 H, H6); 6.7 (s, 1 H, H1'); 5.7 (d, 1 H, H5); 3.6 (s, 3 H, $OCH_3$).

EXAMPLE 10

2-Thio-S-(aceton-1-yl)-1-(3',5'-di-O-benzoyl-2'-O-methyl-β-D-ribofuranosyl)-pyrimidin-4-one Chloroacetone (0.35 ml, 4.35 mmol) was added to a solution of 2-thio-1-(3',5'-di-O-benzoyl-2'-O-methyl-β-D-ribofuranosyl)-pyrimidin-4-one in dichloromethane (920 ml) and triethylamine (0.81 ml, 5.8 mmol). After 16 hrs water was added and the organic layer washed, dried with $Na_2SO_4$, filtered and evaporated to yield the product as a homogeneous material by TLC. $^1$H-NMR ($CDCl_3$): δ 7.5 (d, 1 H, H6); 6.0 (s, 1 H, H1'); 5.8 (d, 1 H, H5); 4.05 (s, 1 H, $CH_2$); 3.4 (s, 3 H, $OCH_3$); 2.3 (s, 3 H, $COCH_3$).

EXAMPLE 11

2-(Aceton-1-yl)-1-(3',5'-di-O-benzoyl-2'-O-methyl)-β-D-ribofuranosyl)pyrimidin-4-one Crude 2-thio-S-(aceton-1-yl)-1-(3',5'-di-O-benzoyl-2'-O-methyl-β-D-ribofuranosyl)-pyrimidin-4-one was dissolved in toluene (20 ml) and triphenylphosphine and potassium t-butoxide (0.29 ml of a 1N solution in THF, Aldrich) was added. The mixture was stirred at 125° C. overnight. The solvent was evaporated and the residue was purified by flash column chromatography (5 cm; chloroform/ethyl acetate, 2:1) to give the product as a slightly yellowish foam (1.26 g, 80% from starting 2-thiouracil). $^1$H-NMR ($CDCl_3$): δ 13.9 (b m, 1 H, N..H..O); 7.25 (s, 3 H, $CH_3$); 4.98 (s, 1 H, CH); 3.5 (s, 3 H, $OCH_3$); 2.2 (s, 1 H, $COCH_3$).

EXAMPLE 12

2-(Hexan-2-on-1-yl)-1-{2'-deoxy-3'-O-[(tert-butyl)diphenyl-silyl]-β-D-erythro-furanosyl}-pyrimidin-4-one 2-Hexanone (1.50 ml, 12 mmol) in THF (60 ml) was cooled to −70° C. Lithium diisopropyamide (2M sol in THF, Aldrich) was added and the solution was stirred for 20 min maintaining the −70° C. temperature. The solution was warmed to room temperature and O2,5'-anhydro-3'-O-(tert-butyldiphenylsilyl)thymidine (1.74 g, 3.76 mmol) was added. The resulting solution became yellowish and after 35 min TLC indicated complete reaction. Water was added and the mixture neutralized carefully with 1N HCl (alternately 3N acetic acid or 1N $H_2SO_4$ can be used). The reaction mixture was partitioned between ether (150 ml) and water (50 ml) and layers separated. The organic layer was dried over $Na_2SO_4$, filtered and evaporated. The residue was purified by flash column chromatography (5 cm, ethylacetate) to yield the product as a slightly yellowish foam (1.47 g, 69%). $^1$H-NMR ($CDCl_3$): δ 14.1 (s, 1 H, N..H..O); 5.8 (m, 1 H, H-1'); 4.8 (s, 1 H, CH); 2.3 (m, 1 H, $CH_2$); 1.8 (m, 2 H, OH & $CH_3$ 5-pyr); 1.4, 1.6 (m, 4 H, $CH_2$); 0.9 (t, 3 H, $CH_3$ chain).

EXAMPLE 13

2-(Hexan-2-on-1-yl)-1-(2'-deoxy-β-D-erythro-furanosyl)-pyrimidin-4-one 2-(Hexan-2-on-1-yl)-1-{2'-deoxy-3'-[(tert-butyl)-diphenylsilyl]-β-D-erythro-furanosyl}-pyrimidin-4-one in THF was deblocked with tetrabutylammonium fluoride (Bu$_4$NF) using standard conditions (see, e.g., Greene and Wuts in *Protective Groups in Organic Synthesis*, 2d ed., John Wiley & Sons, Inc., 1991, p. 83) to give the title compound. $^1$H-NMR (CDCl$_3$): δ 14.3 (s, 1 H, N..H..O); 5.8 (t, 1 H, H1'); 5.35, 5.15 (d,t, 2 H, 3' OH & 5' OH).

EXAMPLE 14

2-Butyl-1-{2'-deoxy-3'-O-[(tert-butyl)diphenylsilyl]-β-D-erythro-furanosyl}-pyrimidin-4-one A solution of O-2,5'-anhydro-3'-O-(tert-butyldiphenylsilyl)thymidine (0.87 g, 1.88 mmol) in THF (50 ml) was cooled to −70° C. and butyllithium (3.75 ml of a 1.6M solution in hexanes, Aldrich) was added. The mixture turned dark yellow immediately. TLC after 30 mins indicated complete reaction. The reaction mixture was warmed to room temperature, quenched with water (5 ml) and neutralized with 0.1N HCl. The mixture was extracted with ether, the organic phase washed with H$_2$O, dried over Na$_2$SO$_4$ and evaporated to give a yellow oil (1.08 g). The oil was further purified by flash column chromatography (3 cm, chloroform/methanol 9:1) to give the product as a yellow foam (0.77 g, 79%). $^1$H-NMR (CDCl$_3$): δ 6.1 (t, 1 H, H1'); 2.9 (t, 2 H, CH$_2$); 2.5 (br m, 1 H, 5' OH); 1.9 (s, 3 H, CH$_3$ pyr); 1.7, 1.4 (m, 4 H, CH$_2$); 0.9 (t, 3 H, CH$_3$ chain).

EXAMPLE 15

2-Methyl-1-(2', 3',5'-tri-O-benzoyl-β-D-ribofuranosyl)pyrimidin-4 -one

2-Methylpyrimidin-4-one (4.42 g, 40 mmol) and a few crystals of ammonium sulfate were refluxed in HMDS overnight. After cooling to room temperature the colorless solution was evaporated. A solution of 1-O-acetyl-2,3,5-tri-O-benzoyl-β-D-ribose (40 mmol, 20.18 g) in 1,2-dichloroethane (200 ml) was added to the residue. Trimethylsilyl trifluoromethanesulfonate (TMSOTfl, 9.78 g, 44 mmol) was added and the resulting clear solution was stirred at room temperature for 2 hrs. The reaction mixture was poured in to saturated NaHCO$_3$ (300 ml) and extracted with chloroform (2×200 ml). The organic phase was evaporated to give a colorless homogeneous foam (23.04 g, 104%, pure by NMR).

EXAMPLE 16

2-Methyl-1-(-β-D-ribofuranosyl)pyrimidin-4-one

To a solution of 2-methyl-1-(2',3',5'-tri-O-benzoyl-β-D-ribofuranosyl)-pyrimidin-4-one (13.86 g, 25 mmol) in methanol (150 ml) was added 4.37N sodium methoxide solution in MeOH (2.5 mmol, 0.1 eq.). The solution was stirred overnight at room temperature and then evaporated. The residue was partitioned between water (100 ml) and dichloromethane (2×150 ml). The aqueous layer was neutralized with Dowex 50 H$^+$-form and evaporated. The orange oily residue was crystallized from ethanol/acetone 3:1 to give the title compound (2.37 g, 39%). $^1$H-NMR (CDCl$_3$): δ 8.1 (d, 1 H, H6); 6.0 (d, 1 H, H5); 5.65 (m, 2 H, H1', 2'-OH); 5.25, 5.2 (d,t, 2 H, 3'-OH, 5'-OH); 2.45 (s, 3 H, CH$_3$).

EXAMPLE 17

5-[(tert-Butyl)dimethylsilyl]-2,3-isopropylidene-D-ribono-1,4-lactone

The title compound was prepared in a manner similar to the preparation of 5-[(tert-butyl)diphenylsilyl]-2,3-isopropylidene-D-ribono-1,4-lactone as reported by Piccirilli, et al., *Helvetica Chimica Acta* 1991, 74, 397–406, substituting 5-(tert-butyl)diphenylsilyl chloride for the 5-(tert-butyl)diphenylsilyl chloride. The product was obtained as a crystalline compound.

EXAMPLE 18

3-{5'-O-[(tert-Butyl)dimethylsilyl]-1'-hydroxyl-2',3'-O-isopropylidene-D-ribofuranosyl}-2-chloro-6-methoxy-pyridine and 5-{5'-O-[(tert-Butyl)dimethylsilyl]-1'-hydroxyl-2',3'-O-isopropylidene-D-ribofuranosyl}-2-chloro-6-methoxy-pyridine Lithium diisopropyamide (12.6 mmol, 6.3 ml of a 2M solution) was added to THF (30 ml) at −70° C. To the resulting solution was added 2-chloro-6-methoxypyridine (1.5 g, 1.25 ml, 10.50 mmol) and the resulting orange, clear solution was stirred at −70° C. in a dry ice bath for 45 mins during which time the solution slowly turned yellow. 5-[(tert-Butyl)dimethylsilyl]-2,3-isopropylidene-D-ribono-1,4-lactone (1.44 g, 5.25 mmol) was added and after 30 mins the dry ice bath was removed and the reaction mixture slowly turned brown as it warmed to room temperature. After 3 hrs at room temperature the reaction was quenched with water and extracted with ether. The combined organic phase was washed with brine, dried over MgSO$_4$ and evaporated to give a yellow oil (2.28 g) of a mixture of the α and β isomers of the title compounds.

EXAMPLE 19

3-{5'-O-[(tert-Butyl)dimethylsilyl]-2',3'-O-isopropylidene-D-ribofuranosyl}-2-chloro-6-methoxy-pyridine To a solution of the isomeric mixture of the above 1'-hydroxy compounds in toluene under N$_2$ in an ice bath will be added triethylsilane (Et$_3$SiH, 2 equiv.) and BF$_3$.Et$_2$O. The mixture is stirred and allowed to come to room temperature. After 2 hours the mixture will be chromatographed on a silica gel column eluted with ethyl acetate/hexanes. The fractions containing the desired 3 β isomer are pooled to yield the product.

EXAMPLE 20

3-{5'-O-[(tert-Butyl)dimethylsilyl]-2',3'-O-isopropylidene-β-D-ribofuranosyl}-2-(1-hexyl-1-yl)-6-methoxy-pyridine A suspension of bis-triphenylphosphine palladium (II) and copper (I) iodide in THF under argon is stirred for 10 mins. To this suspension will be added 1-hexyne and triethylamine. The resulting suspension will be stirred for an additional 10 mins followed by the addition of 3-{5'-O-[(tert-butyl)dimethylsilyl]-2',3'-O-isopropylidene-D-ribofuranosyl}-2-chloro-6-methoxy-pyridine. The resulting mixture is stirred for 1 hr, filtered and evaporated. The residue is dissolved in diethylether, treated with cold 0.1N HCl and the organic phase is dried over MgSO$_4$. Evaporation of the organic phase will yield the title compound.

EXAMPLE 21

2-(2-Amino-1-hexen-1-yl)-3-{5'-O-[(tert-Butyl) dimethylsilyl]-2',3'-O-isopropylidene-β-D-ribofuranosyl}-6-methoxy-pyridine 3-{5'-O-[(tert-Butyl)dimethylsilyl]-2',3'-O-isopropylidene-D-ribofuranosyl)-2-(1-hexyl-1-yl)-6- methoxypyridine will be treated in a pressure bottle with methanolic ammonia (saturated at −20° C.) for 18 hours with stirring. The solvent will be evaporated and the residue purified by flash chromatography to give the title compound.

EXAMPLE 22

2-(2-Amino-1-hexen-1-yl)-3-(2',3'-O-isopropylidene-β-D-ribofuranosyl}-6-methoxy-pyridine 2-(2-Amino-1-hexen-1-yl)-3-{5'-O-[(tert-butyl)-dimethylsilyl]-2',3'-O-isopropylidene-D-ribofuranosyl}-6-methoxypyridine in THF will be treated with Bu$_4$NF at room temperature for 30 mins. The resulting solution will be evaporated and the residue chromatographed on silica gel eluted with MeOH/CHCl$_2$ to give the title compound.

EXAMPLE 23

2-(2-Amino-1-hexen-1-yl)-3-{β-D-ribofuranosyl}-pyrid-6-one 2-(2-Amino-1-hexen-1-yl)-3-(2',3'-O-isopropylidene-β-D-ribofuranosyl}-6-methoxy-pyridine will be dissolved in water and treated with 1N HCl to remove the isopropylidene groups and concurrently hydrolyze the methoxy function to the corresponding 6-pyridone. The resulting solution is extracted with CH$_2$Cl$_2$, the organic phase is washed with saturated bicarbonate, dried over MgSO$_4$ and evaporated. The residue is purified by chromatography on a silica gel column. The product containing fractions will be pooled and evaporated to yield the title compound.

EXAMPLE 24

3,5-[O-(1,1,3,3-Tetraisopropyl)-1,3-disiloxanediyl]-D-ribono-1,4-lactone

D-Ribono-1,4-lactone and 1,3-dichloro-1,1,3,3-tetraisopropyldisiloxane are stirred together in dry pyridine for 16 hrs at 25° C. The solvent is evaporated and the resulting oil will be dissolved in CH$_2$Cl$_2$, washed with saturated sodium bicarbonate and the organic layer added to a silica gel column. The product is eluted from the column with methylene chloride/methanol and the appropriate fractions, combined and evaporated to yield the title compound.

EXAMPLE 25

2-O-Methyl-3,5-[-O-(1,1,3,3-tetraisopropyl)-1,3-disiloxanediyl]-D-ribono-1,4-lactone 3,5-[O-(1,1,3,3-Tetraisopropyl)-1,3-disiloxanediyl]-D-ribono-1,4-lactone will be treated with CH$_3$I and Ag$_2$O at 40° C. overnight generally in accordance with the procedure of Inoue, et al., *Nucleic Acids Research* 1987, 15, 6131 to give the title compound.

EXAMPLE 26

3-{2-O-Methyl-3,5-[-O-(1,1,3,3-tetraisopropyl)-1,3-disiloxane-diyl]-D-ribofuranosyl}-2-chloro-6-methoxy-pyridine and 5-{2-O-Methyl-3,5-[-O-(1,1,3,3-tetraisopropyl)-1,3-disiloxanediyl]-D-ribofuranosyl}-2-chloro-6-methoxy-pyridine Lithium diisopropylamide (as a 2M solution) is added to THF (30 ml) at −70° C. To the resulting solution is added 2-chloro-6-methoxypyridine and the resulting solution stirred at −70° C. in a dry ice bath for 45 mins. 2-O-Methyl-3,5-[-O-(1,1,3,3-tetraisopropyl)-1,3-disiloxanediyl]-D-ribono-1,4-lactone will be added and after 30 mins the dry ice bath removed and the reaction mixture slowly allowed to warm to room temperature. After 3 hrs at room temperature the reaction is quenched with water and extracted with ether. The combined organic phase is washed with brine and dried over MgSO$_4$ and evaporated to yield an oil that of a mixture of the α and β isomers of the title compounds.

EXAMPLE 27

3-{2-O-Methyl-3,5-[-O-(1,1,3,3-tetraisopropyl)-1,3-disiloxanediyl]-β-D-ribofuranosyl}-2-chloro-6-methoxy-pyridine To a solution of the isomeric mixture of the corresponding 1'-hydroxy compounds in toluene under N$_2$ in an ice bath is added Et$_3$SiH (2 equiv.) and BF$_3$.Et$_2$O. The mixture is stirred and allowed to come to room temperature. After 2 hours the mixture will be chromatographed on a silica gel column eluted with ethyl acetate/hexanes. The fractions containing the desired 3 β isomer are pooled to yield the product.

EXAMPLE 28

3-{2-O-Methyl-3,5-[-O-(1,1,3,3-tetraisopropyl)-1,3-disiloxanediyl]-β-D-ribofuranosyl}-2-(1-hexyn-1-yl)-6-methoxy-pyridine A suspension of bis-triphenylphosphine palladium (II) and copper (I) iodide in THF under argon is stirred for 10 mins. To this suspension will be added 1-hexyne and triethylamine. The resulting suspension will be stirred for an additional 10 mins followed by the addition of 3-{2-O-methyl-3,5-[-O-(1,1,3,3-tetraisopropyl)-1,3-disiloxanediyl]-D-ribofuranosyl}-2-chloro-6-methoxy-pyridine. The resulting mixture is stirred for 1 hr, filtered and evaporated. The residue is dissolved in diethylether, treated with cold 0.1N HCl and the organic phase is dried over MgSO$_4$. Evaporation of the organic phase will yield the title compound.

EXAMPLE 29

3-{2-O-Methyl-3,5-[-O-(1,1,3,3-tetraisopropyl)-1,3-disiloxanediyl]-β-D-ribofuranosyl}-6-methoxy-2-(2-thiol-1-hexen-1-yl)-pyridine 3-{2-O-Methyl-3,5-[-O-(1,1,3,3-tetraisopropyl)-1,3-disiloxanediyl]-D-ribofuranosyl}-2-(1-hexyl-1-yl)-6-methoxypyridine in THF will be treated with a steady stream of H$_2$S for 3 mins with stirring. The solvent will be evaporated and the residue purified by flash chromatography to give the title compound.

EXAMPLE 30

3-(2-O-Methyl-β-D-ribofuranosyl)-2-(2-thiol-1-hexen-1-yl)-pyrid-6-one

3-{2-O-Methyl-3,5-[-O-(1,1,3,3-tetraisopropyl)-1,3-disiloxanediyl]-D-ribofuranosyl}-6-methoxy-2-(2-thiol-1-hexen-1-yl)-pyridine will be treated with 3N HCl to remove the tetraisopropyldisiloxanediyl protecting group and hydrolyze the 6-methoxy moiety. The resulting solution will extracted with CH$_2$Cl$_2$ washed with saturated bicarbonate, dried over MgSO$_4$ and the organic phase evaporated. The residue will be chromatographed on silica gel eluted with MeOH/CHCl$_2$ to give the title compound.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A compound of the structure:

wherein:

$R_5$ is H or $CH_3$;

one of $R_2$ and $R_4$ is =O, =NH, or =$NH_2^+$; and the other of $R_2$ and $R_4$ is Q, =$C(R_A)$—Q, $C(R_A)(R_B)$—$C(R_C)(R_D)$—Q, $C(R_A)$=$C(R_C)$—Q or C≡C—Q;

$R_A$, $R_B$, $R_C$ and $R_D$ independently are H, SH, OH, $NH_2$, or $C_1$–$C_{20}$ alkyl, or one of $(R_A)(R_B)$ or $(R_C)(R_D)$ is =O;

Q is hydrogen, $C_1$–$C_{20}$ alkyl, $C_1$–$C_{20}$ alkylamine, $C_1$–$C_{20}$ alkyl-N-phthalimide, $C_1$–$C_{20}$ alkylimidazole, $C_1$–$C_{20}$ alkylbis-imidazole, $NH_2$, $C_2$–$C_{20}$ alkenyl, $C_2$–$C_{20}$ alkynyl, hydroxyl, thiol, keto, carboxyl, a nitrate, nitro, nitroso, nitrile, trifluoromethyl, trifluoromethoxy, O-alkyl, S-alkyl, NH-alkyl, N-dialkyl, O-aralkyl, S-aralkyl, NH-aralkyl, azido, hydrazino, hydroxylamino, isocyanato, sulfoxide, sulfone, sulfide, disulfide, silyl, O-(hydroxyl protecting group), a leaving group, a heterocycle, a polyamine, a polyamide, or a polyether;

$T_3$ and $T_5$ independently are H, phosphate, an activated phosphate, a hydroxyl protecting group, a nucleoside, a nucleotide, an oligonucleotide comprising up to 50 nucleosides joined together by 3'–5' internucleoside linkages, or an oligonucleoside comprising up to 50 nucleosides joined together by 3'–5' internucleoside linkages;

$X_1$ and $X_2$ independently are hydrogen, halogen, hydroxyl, O-(hydroxyl protecting group), thiol, carboxyl, nitrate, nitro, nitroso, nitrile, trifluoromethyl, trifluoromethoxy, O-alkyl, S-alkyl, NH-alkyl, N-dialkyl, O-aralkyl, S-aralkyl, amino, azido, hydrazino, hydroxylamino, isocyanato, sulfoxide, sulfone, sulfide, disulfide, silyl, heterocyclic, alicyclic, carbocyclic, a polyamine, a polyamide, or a polyether; or $T_3$ and one of $X_1$ or $X_2$, together, form a hydroxyl protecting group; and provided that when $T_5$ is a hydroxyl protecting group or together $T_3$ and one of $X_1$ or $X_2$ is a hydroxyl protecting group, then $R_2$ is not $CH_3$; and that when $T_3$ and $T_5$ are H or benzoyl, then $R_2$ is not $CH_2OC_6H_5$; and that when $R_4$ is Q, then Q is not hydroxyl, thiol, amino or hydrogen.

2. A compound of claim 1 wherein one of $X_1$ and $X_2$ is hydrogen and the other is hydroxyl.

3. A compound of claim 1 wherein both of $X_1$ and $X_2$ are hydrogen.

4. A compound of claim 1 wherein $R_2$ is chlorine.

5. A compound of claim 1 wherein $R_4$ is =O.

6. A compound of claim 1 wherein $R_5$ is H.

7. A compound of claim 1 wherein $R_5$ is $CH_3$.

8. A compound of claim 1 wherein $T_3$ and $T_5$ are both H.

9. A compound of claim 1 wherein $T_3$ is an activated phosphate and $T_5$ is a hydroxyl protecting group.

10. A compound of claim 1 wherein at least one of $T_3$ or $T_5$ is an oligonucleotide or an oligonucleoside.

11. A compound of claim 1 wherein one of $R_2$ or $R_4$ is $C(R_A)(R_B)$—$C(R_C)(R_D)$—Q.

12. A compound of claim 11 wherein $R_A$ and $R_B$ are both hydrogen, and $(R_C)(R_D)$ is =O.

13. A compound of claim 12 wherein Q includes a sulfur containing heterocycle and a linking group covalently bound between said C(O) and said sulfur containing heterocycle.

14. A compound of claim 12 wherein said linking group is $C_1$–$C_6$ alkyl, $C_2$–$C_{20}$ alkenyl or $C_2$–$C_{20}$ alkynyl.

15. A compound of claim 1 wherein one of $R_2$ or $R_4$ is $C(R_A)$=$C(R_C)$—Q.

16. A compound of claim 15 wherein $R_A$ is OH, SH or $NH_2$; and $R_C$ is hydrogen.

17. A compound of claim 16 wherein Q is $C_1$–$C_{20}$ alkyl.

18. A compound of claim 16 wherein Q is $C_1$–$C_6$ alkyl.

19. A compound of the structure:

wherein:

$R_5$ is H or $CH_3$;

one of $R_2$ and $R_4$ is =O, =NH, or =$NH_2^+$; and the other of $R_2$ and $R_4$ is =$C(R_A)$—Q, $C(R_A)(R_B)$—$C(R_C)(R_D)$—Q or $C(R_A)$=$C(R_C)$—Q;

$R_A$, $R_B$, $R_C$ and $R_D$ independently are H, SH, OH or $NH_2$, or one of $(R_A)(R_B)$ or $(R_C)(R_D)$ is =O;

Q is halogen, hydrogen, $C_1$–$C_{20}$ alkyl, $C_1$–$C_{20}$ alkylamine, $C_1$–$C_{20}$ alkyl-N-phthalimide, $C_1$–$C_{20}$ alkylimidazole, $C_1$–$C_{20}$ alkylbis-imidazole, or $NH_2$;

$T_3$ and $T_5$ independently are H, phosphate, an activated phosphate, hydroxyl protecting group, a nucleoside, a nucleotide, an oligonucleotide comprising up to 50 nucleosides joined together by 3'–5' internucleoside linkages, or an oligonucleoside comprising up to 50 nucleosides joined together by 3'–5' internucleoside linkages;

$X_1$ and $X_2$ independently are hydrogen, hydroxyl or O-(hydroxyl protecting group); or $T_3$ and one of $X_1$ or $X_2$, together, form a hydroxyl protecting group; and provided that when $T_5$ is a hydroxyl protecting group or together $T_3$ and one of $X_1$ or $X_2$ is a hydroxyl protecting group, then $R_2$ is not $CH_3$; and that when $T_3$ and $T_5$ are H or benzoyl, then $R_2$ is not $CH_2OC_6H_5$ and the when $R_4$ is Q, Q is not hydrogen, hydroxyl, thiol, amino or hydrogen.

20. A compound of claim 19 wherein one of $X_1$ and $X_2$ is hydrogen and the other is hydroxyl.

21. A compound of claim 19 wherein both of $X_1$ and $X_2$ are hydrogen.

22. A compound of claim 20 wherein $R_2$ is chlorine.

23. A compound of claim 19 wherein $R_4$ is =O.

24. A compound of claim 19 wherein $R_5$ is H.

25. A compound of claim 19 wherein $R_5$ is $CH_3$.

26. A compound of claim 19 wherein $T_3$ and $T_5$ are both H.

27. A compound of claim 19 wherein $T_3$ is an activated phosphate and $T_5$ is a hydroxyl protecting group.

28. A compound of claim 19 wherein at least one of $T_3$ or $T_5$ is an oligonucleotide or an oligonucleoside.

29. A compound of claim 19 wherein one of $R_2$ or $R_4$ is $C(R_A)(R_B)$—$C(R_C)(R_D)$—Q.

30. A compound of claim 29 wherein $R_A$ and $R_B$ are both hydrogen; and $(R_C)(R_D)$ is =O.

31. A compound of claim 19 wherein one of $R_2$ is or $R_4$ is $C(R_A)$=$C(R_C)$—Q.

32. A compound of claim 31 wherein $R_A$ is OH, SH or $NH_2$; and $R_C$ is hydrogen.

33. An oligonucleoside comprising up to 50 nucleosides joined together by 3'–5' internucleoside linkages, at least one of said nucleosides having the structure:

wherein:

$R_5$ is H or $CH_3$;

one of $R_2$ and $R_4$ is =O, =NH, or =$NH_2^+$; and the other of $R_2$ and $R_4$ is Q, $C(R_A)(R_B)$—$C(R_C)(R_D)$—Q, $C(R_A)$=$C(R_C)$—Q or C≡C—Q;

$R_A$, $R_B$, $R_C$ and $R_D$ independently are H, SH, OH, NH2 or $C_1$–$C_{20}$ alkyl, or one of $(R_A)(R_B)$ or $(R_C)(R_D)$ is =O;

Q is hydrogen, $C_1$–$C_{20}$ alkyl, $C_1$–$C_{20}$ alkylamine, $C_1$–$C_{20}$ alkyl-N-phthalimide, $C_1$–$C_{20}$ alkylimidazole, $C_1$–$C_{20}$ alkylbis-imidazole, $C_2$–$C_{20}$ alkenyl, $C_2$–$C_{20}$ alkynyl, hydroxyl, thiol, keto, carboxyl, a nitrate, nitro, nitroso, nitrile, trifluoromethyl, trifluoromethoxy, O-alkyl, S-alkyl, NH-alkyl, N-dialkyl, O-aralkyl, S-aralkyl, amino, azido, hydrazino, hydroxylamino, isocyanato, sulfoxide, sulfone, sulfide, disulfide, silyl, O-(hydroxyl protecting group), a leaving group, a heterocycle, a polyamine, a polyamide, or a polyether;

$X_1$ and $X_2$ independently are hydrogen, halogen, hydroxyl, O-(hydroxyl protecting group), thiol, carboxyl, nitrate, nitro, nitroso, nitrile, trifluoromethyl, trifluoromethoxy, O-alkyl, S-alkyl, NH-alkyl, N-dialkyl, O-aralkyl, S-aralkyl, amino, azido, hydrazino, hydroxylamino, isocyanato, sulfoxide, sulfone, sulfide, disulfide, silyl, heterocyclic, alicyclic, carbocyclic, a polyamine, a polyamide, or a polyether; and $T_3$ and $T_5$ independently are H, a nucleoside or an oligonucleoside, provided that $T_3$ and $T_5$ are not both H.

34. An oligonucleoside containing at least one nucleoside of the structure:

wherein:

$R_5$ is H or $CH_3$;

one of $R_2$ and $R_4$ is =O, =NH, or =$NH_2^+$; and the other of $R_2$ and $R_4$ is $C(R_A)(R_B)$—$C(R_C)(R_D)$—Q or $C(R_A)$=$C(R_C)$—Q;

$R_A$, $R_B$, $R_C$ and $R_D$ independently are H, SH, OH or $NH_2$, or one $(R_A)(R_B)$ or $(R_C)(R_D)$ is =O;

Q is halogen, hydrogen, $C_1$–$C_{20}$ alkyl, $C_1$–$C_{20}$ alkylamine, $C_1$–$C_{20}$ alkyl-N-phthalimide, $C_1$–$C_{20}$ alkylimidazole, $C_1$–$C_{20}$ alkylbis-imidazole, imidazole, bis-imidazole, amine or N-phthalimide;

$X_1$ and $X_2$ independently are hydrogen, hydroxyl or O-(hydroxyl protecting group); and $T_3$ and $T_5$ independently are H, a nucleoside, or an oligonucleoside that is joined to said structure.

35. A compound of the structure:

wherein:

J is N or CH;

$R_4$ is —OH, —$NH_2$, or —$NH_3^+$;

$R_2$ is Q, =$C(R_A)$—Q, $C(R_A)(R_B)$—$C(R_C)(R_D)$—Q, $C(R_A)$=$C(R_C)$—Q or C≡C—Q;

$R_A$, $R_B$, $R_C$ and $R_D$ independently are H, SH, OH, NH2 or $C_1$–$C_{20}$ alkyl, or one of $(R_A)(R_B)$ or $(R_C)(R_D)$ is =O;

Q is hydrogen, $C_1$–$C_{20}$ alkyl, $C_1$–$C_{20}$ alkylamine, $C_1$–$C_{20}$ alkyl-N-phthalimide, $C_1$–$C_{20}$ alkylimidazole, $C_1$–$C_{20}$ alkylbis-imidazole, $NH_2$ $C_2$–$C_{20}$ alkenyl, $C_2$–$C_{20}$ alkynyl, hydroxyl, thiol, keto, carboxyl, a nitrate, nitro, nitroso, nitrile, trifluoromethyl, trifluoromethoxy, O-alkyl, S-alkyl, NH-alkyl, N-dialkyl, O-aralkyl, S-aralkyl, azido, hydrazino, hydroxylamino, isocyanato, sulfoxide, sulfone, sulfide, disulfide, silyl, O-(hydroxyl protecting group), a leaving group, a heterocycle, a polyamine, a polyamide, or a polyether;

$T_3$ and $T_5$ independently are H, phosphate, an activated phosphate, hydroxyl protecting group, a nucleoside, a nucleotide, an oligonucleotide comprising up to 50 nucleosides joined together by 3'–5' internucleoside linkages, or an oligonucleoside comprising up to 50 nucleosides joined together by 3'–5' internucleoside linkages; and $X_1$ and $X_2$ independently are hydrogen, halogen, hydroxyl, O-(hydroxyl protecting group), thiol, carboxyl, nitrate, nitro, nitroso, nitrile, trifluoromethyl, trifluoromethoxy, O-alkyl, S-alkyl, NH-alkyl, N-dialkyl, O-aralkyl, S-aralkyl, amino, azido, hydrazino, hydroxylamino, isocyanato, sulfoxide, sulfone, sulfide, disulfide, silyl, heterocyclic, alicyclic, carbocyclic, a polyamine, a polyamide, or a polyether.

36. A method of preparing a compound according to claim 1, comprising contacting a 2,2'-anhydropyrimidine with a nucleophile having formula —OH, —NH$_2$, —CH(R$_A$)—O, —C(R$_A$)(R$_B$)—C(R$_C$(R$_D$)—Q, —CH(R$_A$)=C(R$_C$)—Q, —C≡C—O, —F, —Cl, —Br, —I, —N-imidazole, —N-bis-imidazole, —N-phthalimide, —SH, —NO$_3$, —NO$_2$, —NO, —OCF$_3$, —O-alkyl, —S-alkyl, —NH-alkyl, —N-dialkyl, —O-aralkyl. —S-aralkyl, —NH-aralkyl, —N$_3$, —NHNH$_2$, —NHOH, —NCO, —SO$_2$H, —SO$_3$H, or —SSH under conditions effective to form a covalent bond between said nucleophile and the 2-position of said pyrimidine.

37. A method of preparing a compound according to claim 1, comprising contacting a 2,5'-anhydropyrimidine with a nucleophile having formula —OH, —NH$_2$, —CH(R$_A$)—Q, —C(R$_A$)(R$_B$)—C(R$_C$)(R$_D$)—Q, —CH(R$_A$)=C(R$_C$)—Q, —C≡C—Q, —F, —Cl, —Br, —I, —N-imidazole, —N-bis-imidazole, —N-phthalimide, —SH, —NO$_3$, —NO$_2$, —NO, —OCF$_3$, —O-alkyl, —S-alkyl, —NH-alkyl, —N-dialkyl, —O-aralkyl, —S-aralkyl, —NH-aralkyl, —N$_3$, —NHNH$_2$, —NHOH, —NCO, —SO$_2$H, —SO$_3$H, or —SSH under conditions effective to form a covalent bond between said nucleophile and the 2-position of said pyrimidine.

38. A method of preparing a compound according to claim 1 wherein $R_4$ is C≡C—Q, comprising contacting a 4-halopyrimidine with an alkyne having formula HC≡C—Q in the presence of an organometallic coupling reagent for a time and under reaction conditions effective to form a covalent bond between said alkyne and the 2-position of said pyrimidine.

39. The compound of claim 1 wherein said heterocycle is imidazole, bis-imidazole, or N-phthalimide.

40. The compound of claim 1 wherein said polyether is a polyethylene glycol.

41. A compound of claim 1 wherein Q is halogen.

42. A compound of claim 19 wherein Q is halogen.

43. The compound of claim 33 wherein said heterocycle is imidazole, bis-imidazole, or N-phthalimide.

44. The compound of claim 33 wherein said polyether is a polyethylene glycol.

* * * * *

UNITED STATES PATENT AND TRADEMARK OFFICE
CERTIFICATE OF CORRECTION

PATENT NO. : 6,060,592
DATED : May 9, 2000
INVENTOR(S) : Acevedo et al.

It is certified that error appears in the above-identified patent and that said Letters Patent is hereby corrected as shown below:

Column 6,
Lines 61 and 62, please delete "OH or O-benzoyl" and insert therefor -- H or benzoyl --

Column 9,
Scheme 1, in the "6,8,10,11" please delete "NH" and insert therefore -- $N^H$ --

Signed and Sealed this

Twenty-first Day of January, 2003

JAMES E. ROGAN
*Director of the United States Patent and Trademark Office*